(12) United States Patent
Baddour (10) Patent No.: US 7,118,537 B2
(45) Date of Patent: Oct. 10, 2006

(54) METHOD AND DEVICE FOR COLLECTING AND ANALYZING EXHALED BREATH

(75) Inventor: Alfred R. Baddour, Austin, TX (US)

(73) Assignee: Respiratory Research, Inc., Charlottesville, VA (US)

( * ) Notice: Subject to any disclaimer, the term of this patent is extended or adjusted under 35 U.S.C. 154(b) by 559 days.

(21) Appl. No.: 10/257,912

(22) PCT Filed: Apr. 30, 2001

(86) PCT No.: PCT/US01/13895

§ 371 (c)(1),
(2), (4) Date: Oct. 17, 2002

(87) PCT Pub. No.: WO01/84112

PCT Pub. Date: Nov. 8, 2001

(65) Prior Publication Data

US 2003/0208132 A1    Nov. 6, 2003

(51) Int. Cl.
| | | |
|---|---|---|
| A61B 5/08 | (2006.01) | |
| B65D 81/00 | (2006.01) | |
| A61B 5/02 | (2006.01) | |
| G01N 1/22 | (2006.01) | |
| G01N 31/00 | (2006.01) | |
| G01N 33/497 | (2006.01) | |
| B32B 5/02 | (2006.01) | |
| B32B 27/04 | (2006.01) | |
| B32B 27/12 | (2006.01) | |

(52) U.S. Cl. ..................... 600/543; 600/532
(58) Field of Classification Search ............... None
See application file for complete search history.

(56) References Cited

U.S. PATENT DOCUMENTS

| | | | |
|---|---|---|---|
| 4,947,861 A | | 8/1990 | Hamilton |
| 5,026,027 A | | 6/1991 | Hamilton |
| 6,033,368 A | * | 3/2000 | Gaston et al. ............... 600/532 |
| 6,579,257 B1 | * | 6/2003 | Elgas et al. .................. 604/67 |
| 6,585,661 B1 | * | 7/2003 | Hunt et al. ................. 600/532 |
| 6,631,713 B1 | * | 10/2003 | Christopher ........... 128/200.21 |

FOREIGN PATENT DOCUMENTS

WO             95/31721     * 11/1995    ................. 600/532

* cited by examiner

*Primary Examiner*—Robert L. Nasser
(74) *Attorney, Agent, or Firm*—Woods, Rogers PLC; Peter E. Rosden (57) ABSTRACT

A method and device for collecting, storing, shipping, preparing and analyzing condensate derived from the exhaled breath of a user. Using the mouthpiece (15) of the device (10), a human subject inhales drawing air through a check valve (30).

17 Claims, 6 Drawing Sheets

METHOD AND DEVICE FOR COLLECTING AND ANALYZING EXHALED BREATH

TECHNICAL FIELD

The subject invention relates generally to a method and device for determining medical conditions, and, more particularly to a method and device for condensing, storing, transporting, degassing and analyzing exhaled breath.

BACKGROUND OF THE INVENTION

Recent medical research indicates that human airway acidity and ammonia levels may be indicative of several events including the onset of asthmatic symptoms. Furthermore, this research indicates that the acidity measurements taken from a condensed sample of exhaled breath can be correlated to the actual conditions inside the airway.

Many known devices for collecting condensate from a user's breath rely on gravity to form a condensate pool from which a sample for testing may be drawn. These types of devices require that condensate droplets become large enough to overcome water's naturally tendency to stick to the walls of a collecting tube. Then, when the amount of condensate eventually becomes large enough, a risk of loss of collected condensate sample through seepage out of the collection area may arise due to ineffective sealing of the collection area. Even when an adequate condensate sample had been collected, a risk of contamination occurred due to the necessity to transfer the sample from a collecting tube into test tubes or test devices. Moreover, where the collecting tube is not cooled in some way, condensate formation takes an inordinate amount of time. In some cases, the collecting tube is inserted into an ice bucket or may even be separately cooled by refrigeration systems in order to increase the amount and speed of condensate formation. In other cases, use of a Teflon® collecting tube has been tried to make the tube walls more slippery to enhance the speed and amount of condensate collected. All of these arrangements tend to be either expensive, complicated, ineffective, bulky, inefficient or time-consuming to use. In addition, other condensate collecting and testing devices generally do not provide the ability in a single device both to quickly and efficiently collect condensate while also delivering test substances such as gases or liquids into the condensate without contamination. Moreover, such devices are not typically portable and do not lend themselves easily to use by patients in their own homes. Another disadvantage of devices of the prior art is that they usually do not enable patients to collect condensate samples, prepare those collected samples for testing and then also perform certain tests themselves on the samples.

What is needed is a device and method for condensate collection which solves the problems and shortcoming already described and, in addition, collects a greater amount of condensate from a given amount of exhaled breath in a shorter time than previously possible while also advancing the art by providing a multi-functional valve for use in such a condensate collection device that simultaneously assists in solving several of those problems.

SUMMARY OF THE INVENTION

The present invention relates to a device and method for collecting condensate from air exhaled by a subject user. The device comprises a mouthpiece, a filter housing, a hollow condensate collecting tube, a movable valve inserted within the collecting tube, a cooling sleeve for placement over the collecting tube, means for moving the valve through the collecting tube and a removable airtight cap. In order to practice the method employing the device, the cooling sleeve is cooled to a temperature lower than that of the collecting tube prior to being slid thereover, air is inhaled by a subject user through the mouthpiece and exhaled through the movable valve into the collecting tube. After the passage of between about two and twenty minutes of breathing, the cooling sleeve is removed from around the collecting tube, the movable valve is advanced through the tube thereby wiping away condensate formed on the interior walls of the tube causing that condensate to collect in a pool around the valve. Thereafter, an airtight cap may be placed over the end of the collecting tube nearest the condensate pool in order to seal the collecting tube prior to storage and/or shipment to a testing location. At the test location, the airtight cap is removed and one or more gasses or liquids is introduced into the condensate through the unique structure of the valve as called for by the particular test to be performed on the condensate. In one embodiment of the device, gas is introduced into the condensate in order to remove carbon dioxide and permit the acidity level of the condensate to be reproducibly measured. Testing may be performed after removing samples of the condensate from the collecting tube or by means of a probe placed into contact with the condensate pool or by insertion of chemicals or chemically impregnated strips.

It is a primary objective of this invention to provide a simple self-contained and portable device for efficiently collecting, storing and shipping condensate derived from the exhaled breath of a subject wherein the wettable components of such a device may be disposable.

An additional objective of this invention is to provide a method for collecting condensate derived from the exhaled breath of a subject which is fast, simple, efficient and performable by nonprofessional personnel.

A further objective of this invention is to provide a device and method in which condensate samples collected from the exhaled breath of a user may be both collected and subjected in situ to various laboratory tests, including ones for measuring pH levels, without the risk of contamination by exposure to influences external to a collecting tube.

A yet additional objective of this invention is to provide a condensate collecting device which may be made available for use in a patient's home or workplace.

It is still another objective of this invention to provide a device and multiple methods for removing carbon dioxide from condensate collected from the exhaled breath of a subject preparatory to measuring the acidity of such condensate.

It is yet a further objective of this invention to provide a multipurpose valve structure having a unique elliptical shape for use within a tube for collecting condensate from the exhaled breath of a subject which makes the collection of condensate more efficient and also assists in preparing the collected condensate for laboratory testing.

It is another objective of this invention to provide a device for degassing and/or for adding one or more gasses, liquids or other materials to a sample of condensate collected from the exhaled breath of a subject prior to or while performing laboratory tests on that sample.

A further objective of this invention is to provide a device in which condensate may be collected, stored and transported in a single unit.

Still another objective of this invention is to provide a condensate collecting device which makes septuple use of a valve within the device for preventing the admission of air from a condensate collecting tube during inhalation, admitting exhaled air into the condensate collecting tube, making airflow turbulent, swiping condensate off the interior walls of the tube, preventing efflux of condensate, retaining the condensate in a pool within the tube and channeling gasses or liquids into the condensate.

Yet another objective of this invention is to provide a simple and efficient method for deaerating or degassing collected condensate.

Still a further objective of this invention is to provide a malleable duckbill valve having an elliptical cross-section for placement within a non-malleable tube having a circular cross-section so that a seal is made in the duckbill valve without a pressure gradient across the valve.

A yet additional objective of this invention is to provide a one-way malleable duckbill valve for placement within a condensate collecting tube which encourages turbulent airflow as a subject's exhaled breath passes through.

Another objective of this invention is to provide a hollow duckbill valve permitting a mechanical seal to be obtained between the valve and the nose portion of a probe inserted into the hollow center of the valve.

Yet a further objective of this invention is to provide a hollow duckbill valve incorporating one or more passageways through which gasses or fluids will flow when the valve is subjected to particular mechanical stresses.

An additional objective of this invention is to provide a device with built-in protection for passersby against possible release into the atmosphere of microbes from the lungs of the user of the device.

These and other objects, features and characteristics of the present invention, as well as the methods of operation and functions of the related elements of structure and the combination of parts and economies of manufacture, will become more apparent upon consideration of the following description and the appended claims with reference to the accompanying drawings, all of which form a part of this specification, wherein like reference numerals designate corresponding parts in the various figures. It is to be expressly understood, however, that the drawings are for the purpose of illustration and description only and are not intended as a definition of the limits of the invention.

DETAILED DESCRIPTION OF THE INVENTION

The device of the invention is intended to be used to condense the water normally exhaled in breath by a human subject and to gather this water in such a manner and in such volume that tests may be performed on the condensate. These tests include measuring acidity, ammonia concentration, as well as the concentration of other characteristics, chemicals and compounds of biologic interest. It may be used by an unskilled layperson, then sealed for transport to a laboratory where subsequent analysis may be performed. Alternatively, the device may also function as part of a home or workplace-diagnostic device constructed to accept the device and perform the required measurements automatically. Additionally, it may be used in any setting without additional devices, by adding chemical reagents or test strips to detect chemical features and compounds of interest.

Figure 1:
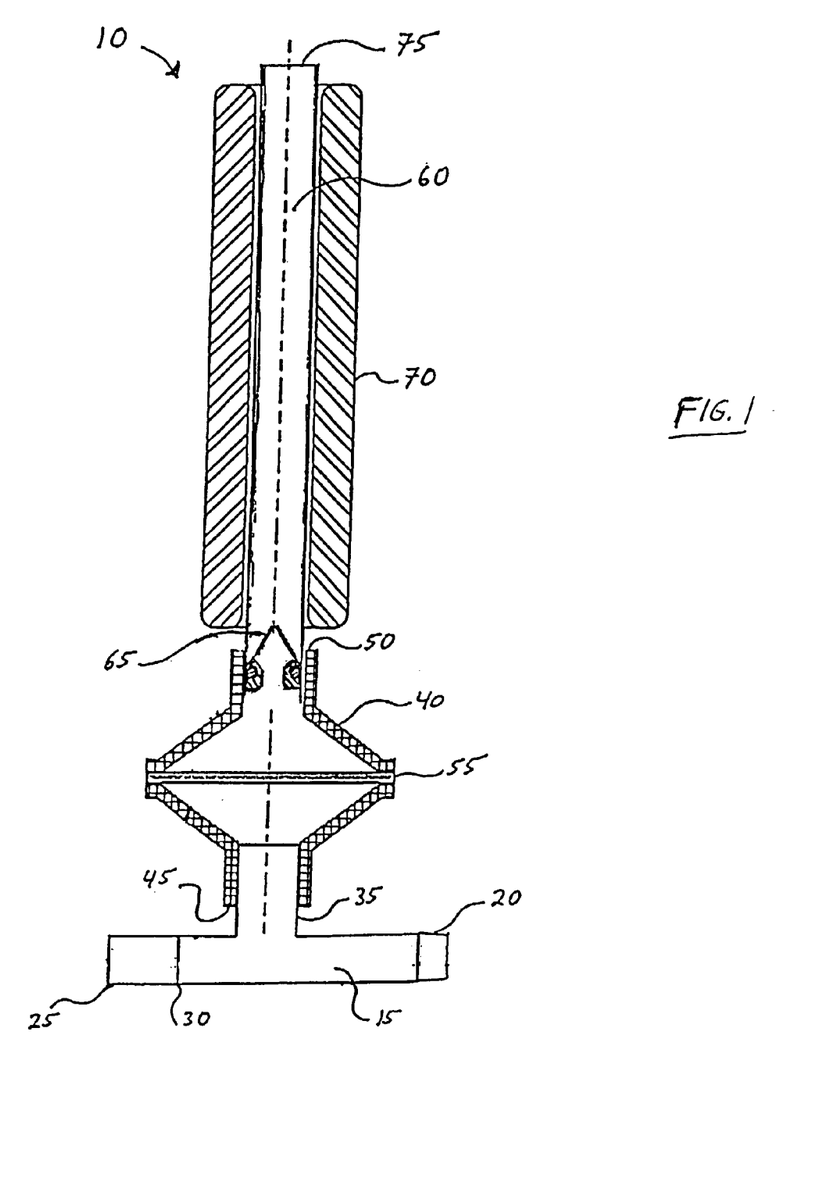
FIG. 1 is a center cross-sectional view of the device of the invention.
Figure 2:
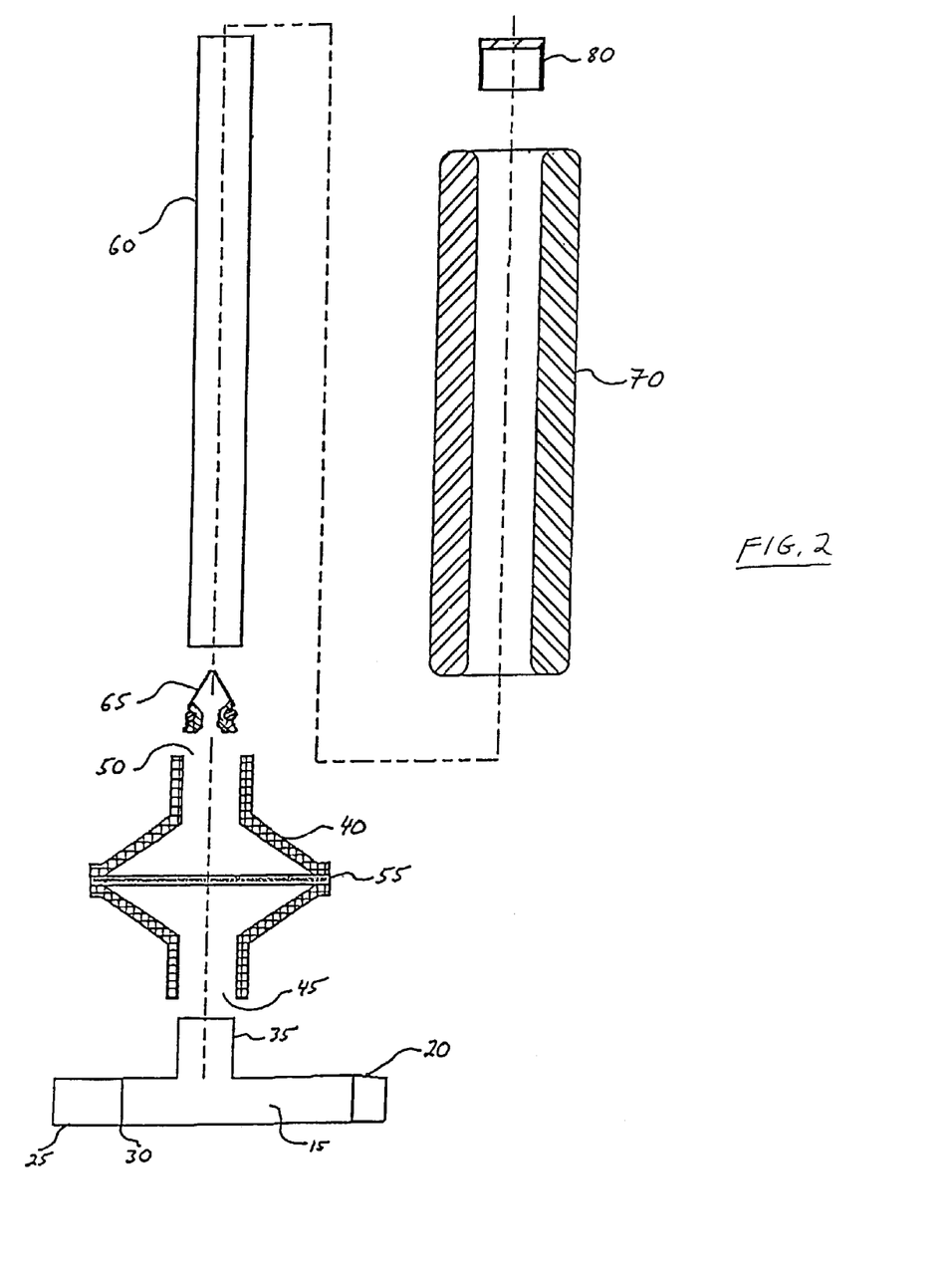
FIG. 2 is a center cross-sectional view of the individual components of the device of the invention in a disassembled state.
Figure 3:
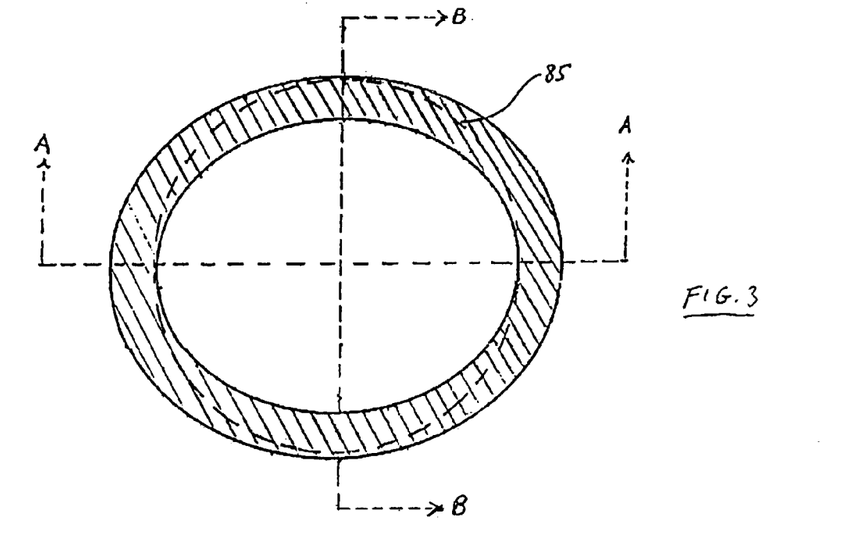
FIG. 3 is a center cross-section view of the duckbill valve of this invention before insertion into a collecting tube along a plane perpendicular to the walls of a collecting tube.
Figure 4:
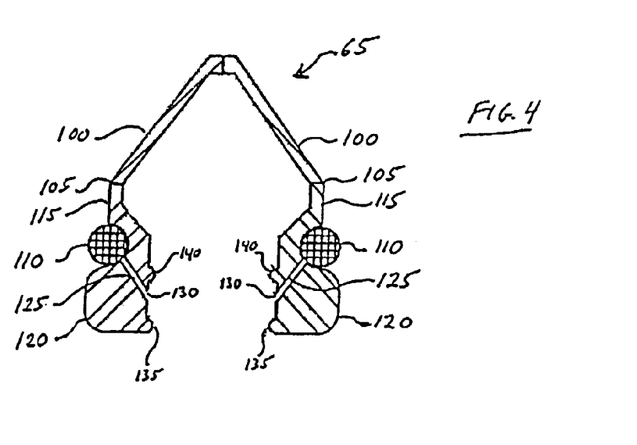
FIG. 4 is a center cross-sectional view of the duckbill valve of this invention along line A—A of FIG. 3.
Figure 5:
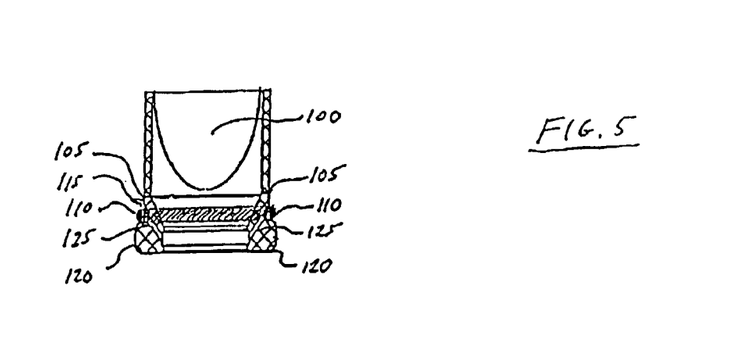
FIG. 5 is a side view of the duckbill valve of this invention.

For a better understanding of the invention, reference is now made to FIG. 1 of the drawings. This figure illustrates a center cross-sectional view of invention device in a dormant state prior to use. Device 10 may be assembled manually from several principal components either before use or on site. Mouthpiece 15 may be a generally tubular T-shaped device with three open projections. On one end, mouthpiece 15 has a generally oblong projection 20 designed to be comfortably inserted between a subject user's lips. The opposite end projection 25 may be generally tubular in shape, is open to the atmosphere and includes a check valve 30 situated nearby for admitting ambient air from the atmosphere through projection 25 into a subject user's mouth and lungs and for preventing an outflow of air through projection 25 during the exhalation process.

Projection 35 is sized so as to be removably insertable into one end of optional filter housing 40 and to be retained therein by virtue of friction between the walls of the exterior of projection 35 and the walls of the interior of the end of filter housing 40 into which it is inserted. Alternatively, projection 35 can be placed in direct intimate contact with the inner or outer surface of collecting tube 60, and retained there by virtue of friction. During exhalation by the subject user, check valve 30 closes and forces exhaled breath to flow through projection 35.

Optional filter housing 40 may comprise a tube-like structure open on both ends and having a filter compartment disposed in the approximate middle thereof separating the two openings 45 and 50 of the tube. Opening 45 on one end of filter housing 40 is sized so as to receive projection 35 from mouthpiece 15. Optional filter housing 40 includes an optional filter assembly 55. In the preferred embodiment, the filter compartment and filter are circular and have a diameter of approximately four times the diameter of opening 50, although other configurations and relative dimensions may be used. Different pore size of the filter might be chosen to limit passage of particles to sizes of particular interest. As particle size might relate to site of formation or other features relevant to the airway, this optional filtering is a useful feature. Optional filter assembly 55 in general functions to remove larger particles from exhaled breath prior to its entering collecting tube 60 and, depending on the filter chosen, also serves to prevent egress of infectious particles in the atmosphere during exhalation. This feature protects passersby from microbes possibly release from the lung of a subject during use of the device. The structure of mouthpiece 15 serves a similar function by substantially reducing the number of salivary droplets which enter optional filter housing 40 or collecting tube 60.

Collecting tube 60 is a straight plastic tube open on both ends with a circular cross-section and may have a length of between approximately 3 inches and 20 inches, preferably about 8.75 inches, and a diameter of approximately ½ inch and at most approximately 2 inches, preferably about 0.875 inches. With tubes smaller than ½ inch in diameter, exhaling becomes difficult for the subject user, while with tubes larger than 2 inches in diameter, condensation efficiency is low. Regardless of the exact dimension used, the diameter of collecting tube 60 may be slightly smaller than that of opening 50 in filter housing 40, or alternatively smaller than that of projection 35, so as to fit retentively within the corresponding neck of filter housing 40 encompassing opening 50 or within projection 35. Alternatively, the diameter of collecting tube 60 may be slightly larger than that of opening 50, or projection 35, so that the neck of filter housing 40 including opening 50, or alternatively projection 35, may be securely and retentively inserted inside one end of collecting tube 60. Collecting tube 60 may also be constructed from other materials such as stainless steel, anodized aluminum, Teflon® and various types of plastics, and functions to collect, condense and store vaporized and aerosolized particles from breath exhaled thereinto.

The exterior of collecting tube 60 may incorporate a writable surface for subject users to identify samples with an indelible marker or other suitable writing instrument. Alternatively, a label with named fields for information could be used or bar coding or other scannable data with identifying or destination information could be imprinted on collecting tube 60 prior to delivery.

Duckbill valve 65 is inserted into the lower end of collecting tube 60 a distance of approximately ½ inch and remains in a closed position when the device is not in use. Duckbill valve 65 may be comprised of rubber or rubber-like elastomeric materials, or plastics which approximate or behave as elastomers, and functions to prevent the passage of air from the end 75 of collecting tube 60 exposed to the atmosphere during the inhaling process described below using mouthpiece 15 and to admit breath from a subject user into collecting tube 60 during the exhaling process, also described below. Its structure and function also prevent the condensate collected in collecting tube 60 from escaping during and after the breath condensate collection procedure.

Cooling sleeve 70 is a hollow tube sized to slide over collecting tube 60 and place the inner walls of cooling sleeve 70 into physical contact or at least close physical proximity with collecting tube 60 shortly prior to and during practice of the method of this invention. Cooling sleeve 70 may be slightly shorter than collecting tube 60 and, when in place, should not extend to a greater height than collecting tube 60. Cooling sleeve 70 may be constructed of a material such as aluminum or any high specific heat, durable, reusable material which does not deteriorate when wet and tends to retain and maintain a low temperature when cooled. In one preferred embodiment, the cooling sleeve might be a container in which chemicals can be mixed that create an endothermic reaction, thus providing substantial cooling.

When placed in position surrounding collecting tube 60 as required for practice of the method of this invention, cooling sleeve 70 functions to draw heat from the inner surface of collecting tube 60, as will be described below, so as to accelerate the condensing process occurring within the tube. In the preferred embodiment, when properly positioned, collecting tube 60 extends on one open end somewhat beyond the corresponding end of cooling sleeve 70 and terminates approximately coequally with the end of cooling sleeve 70 on the other end. Alternatively, collecting tube 60 may extend on the other end beyond the corresponding end of cooling sleeve 70 so as to be insertable into opening 50 of optional filter housing 40.

FIG. 2 provides a center cross-sectional view along a center vertical axis of device 10 of all of the principal components of device 10 in a disassembled state from the component positioned vertically the lowest, mouthpiece 15, to that positioned highest, airtight cap 80. Airtight cap 80 is provided as part of device 10 for secure, retentive placement over open end 75 of collecting tube 60 after the method of the invention has been practiced but prior to storage and/or shipment of collecting tube 60 to a laboratory for analysis of condensate. Together with normally closed duckbill valve 65, airtight cap 80 seals the condensate sample within collecting tube 60 and prevents any fluid exchange with matter or air outside of collecting tube 60. Airtight cap 80 may be formed from malleable plastic or another material, but its composition is not critical to practice of the invention so long as it provides a secure seal with open end 75 when placed thereover. Collecting tube 60, duckbill valve 65 and airtight cap 80 together form a disposable assembly which may be prepackaged for a single use ensuring no complicated cleaning or contamination issues arise from use of device 10.

Duckbill valve 65 is a critical component of device 10. It is uniformly constructed from rubber or a material with resilient, rubber-like properties. FIG. 3 represents a cross-sectional view of duckbill valve 65 taken below valve leaves 100, shown in FIGS. 4 and 5 below, prior to its insertion into collecting tube 60 along a plane perpendicular to the walls of collecting tube 60 were duckbill valve 65 inserted therein. Note that since collecting tube 60 has a circular cross-section, as indicated by dotted line 85, one would normally expect duckbill valve 65 to have a correspondingly circular cross-section. However, its cross-section is uniquely elliptical so that, when forced into a circular shape, such as in the circular bore of collecting tube 60, it will deform disproportionately so as to create a complete seal between the valve leaves 100 of duckbill valve 65, shown in FIGS. 4 and 5 below. This structure provides a seal even at zero reverse differential pressure and is dissimilar from duckbill valves known in the art that require pressure gradients to assure complete valve closure. This feature is particularly valuable in this invention since it assists in providing a secure and long-lasting seal to keep condensate inside collecting tube 60 during long-term storage and/or transport.

FIG. 4 additionally shows a center cross-sectional view of duckbill valve 65 across the center of both leaves 100 of the valve on a plane parallel to the walls of collecting tube 60 along line A—A of FIG. 3. Leaves 100 incorporate malleable structures 105 with which they are attached to section 115 of the body of duckbill valve 65. An opening may be formed along the slit where leaves 100 meet each other. The center of duckbill valve 65 is hollow. Due to the elliptical valve shape constrained in a circular structure, leaves 100 are biased to a closed position along malleable structures 105. Thus, when a subject user is inhaling, leaves 100 prevent the admission of air into mouthpiece 15 through collecting tube 60. However, during exhaling, leaves 100 open along the slit where they meet and admit air into collecting tube 60. The structure of duckbill valve 65 also results in the creation of turbulence during exhalation which helps to improve condensation efficiency along the walls of collecting tube 60. For example, shallow breathing through an empty collecting tube 60 is not very turbulent. But when shallow breathing is directed through duckbill valve 65, leaves 100 open only a little, and leaves 100 vibrate, proving that there is turbulent airflow. When heavier breathing at a higher velocity occurs, leaves 100 open further, preventing increased resistance from occurring while still encouraging turbulence.

During exhalation, particles of airway lining fluid are ripped off the airway wall and carried in the humid airstream out of the body. When the ambient temperature declines below the dew point (i.e. upon egress from the mouth), the gas phase water vapor/water molecules attach themselves onto the small aerosolized particles, enlarging the particles and increasing the chance by inertia that they will strike nearby surfaces such as the interior walls of collecting tube 60, especially where there is turbulent airflow. Thus, the creation of turbulent airflow by duckbill valve 65 is another important feature since it allows fluid particles to impact the inner surface of collecting tube 60, encouraging fluid collection.

Duckbill valve 65 incorporates a notched area around its exterior into which is tightly and sealingly fitted a rubberized Teflon® ring 110 having an exterior diameter just slightly greater than that of the minor axis of the ellipse formed by the footprint of duckbill valve 65 when at rest. Therefore, when ring 110 is in place, it is biased and makes sealing contact with the interior walls of collecting tube 60. Ring 110 may also be composed of materials other than Teflon® such as polypropylene, so long as it functions in the same way as does the Teflon® ring described. This ring serves three functions. First, it is a wiper which, as discussed below, removes condensation from the interior walls of collecting tube 60 after the subject user has completed exhalation. Second, it maintains the alignment of duckbill valve 65 in an orthogonal orientation to the walls of collecting tube 60. Finally, it functions as a valve itself as discussed next.

The lower part of duckbill valve 65 consists of two general sections 115 and 120. There are one or more hollow passageways 125 running diagonally upward from an initiation point 130 within the interior hollow area of duckbill valve 65 through lower section 120 into the circular notched area formed on the exterior of duckbill valve 65. Note that only one passageway 125 is required for subsequent degassification or deaeration steps, although as many as ten such passageways may be preferred depending on the circumstances. Also, note that such passages are not circumferential around the valve, so that in a slightly different cross section, they would not be seen at all, revealing that upper section 115 is confluent with lower section 120 throughout most of the valve structure.

Lower section 120 tends to be stiffer than upper section 115 since there is a greater volume of material in lower section 120 and, unlike section 115, it is constrained from movement by direct contact with the walls of collecting tube 60. Thus, when gas pressure is introduced through passageways 125 against Teflon® ring 110, section 115 has a tendency to deflect allowing the gas to pass around Teflon® ring 110 and into the portion of collecting tube 60 above duckbill valve 65. First inner ring 135 is a bump-like ridge extending around the hollow inner portion of duckbill valve 65 at approximately at its base. Second inner ring 140 is another bump-like ridge extending around the hollow inner portion of duckbill valve 65 at a point displaced slightly above initiation point 130 of any passageway 125. The importance of these features will become clear in conjunction with discussion of the degassing of collecting tube 60 discussed below in conjunction with FIGS. 6 and 7.

FIG. 5 shows a side view of duckbill valve 65 along a plane rotated 90 degrees around a vertical axis from the view shown in FIG. 4. This represents a side view along the plane represented by the line B—B of FIG. 3. As is evident, the valve has a bilateral structural symmetry.

The method of this invention is practiced after device 10 has been assembled as described above and shown in the drawings. Although not a required assembly step, cooling sleeve 70 may be placed in a freezer for approximately 20 to 30 minutes prior to use since the larger the difference in temperature between the walls of cooling sleeve 70 and collecting tube 60 the faster and more efficiently condensation will occur and the greater the amount of condensate produced will be. It is required, however, that cooling sleeve 70 be somewhat cooler than collecting tube 60 prior to beginning to practice the method so that the condensation process will be enhanced. The cooling sleeve 70 can be cooled to various temperatures depending on need. When chilled to 20 degrees C. or below, for example, the exhaled fluid and vapors collect as frozen solid material on the inside of the collecting tube 60, a feature advantageous for the assays of compounds unstable in liquid phase water, as would be the case with a cooling sleeve chilled to a somewhat higher temperature. Temperatures obtained in a home refrigerator or home freezer are satisfactory for excellent liquid phase fluid collection for most purposes, including assessing pH. Throughout practice of the method until after installation of airtight cap 80, it is preferable to keep collecting tube 60 reasonably perpendicular to the ground.

As the first step in the method, referring again for visual reference to FIG. 1, a subject user places projection 20 of mouth piece 15 between his or her lips and inhales. Duckbill valve 65 remains closed due to the bias of flaps 100 and air is admitted into mouthpiece 15 from projection 25 through check valve 30. The subject user then exhales. The stream of exhaled breath is blocked from egress out of projection 25 by check valve 30 and follows the path of least resistance upward through projection 35 into optional filter housing 40, through optional filter assembly 55 and into duckbill valve 65 where leaves 100 are caused to separate and open due to the air pressure allowing the exhaled breath to enter collecting tube 60. When exhalation is complete, leaves 100 return to their naturally biased closed position.

Due to the temperature differential between the exhaled breath and the air inside and the walls of collecting tube 60, the temperature of which has been lowered due to the contact or close proximity of collecting tube 60 with cooling sleeve 70, condensation begins to form on the walls of collecting tube 60 as exhaled breath traverses the length of collecting tube 60. Due to the force of gravity, some condensate tends to run down the walls of collecting tube 60 to form a pool around Teflon® ring 110 at the base of duckbill valve 65. Most remains in place as tiny droplets on the inner wall of collecting tube 60. Meanwhile, the remaining, now dehydrated, exhaled breath is allowed to escape from open end 75 of collecting tube 60 which remains open to the atmosphere. In general, between about two and twenty minutes of breathing will be performed to provide sufficient sample. In preferred embodiments, a set number of breaths, for example ten, will be sufficient.

While keeping collecting tube 60 perpendicular to the ground and the end of collecting tube 60 containing duckbill valve 65 nearest to the ground, cooling sleeve 70 is slid away from collecting tube 60. Then, while keeping collecting tube 60 reasonably perpendicular to the ground and the end of collecting tube 60 containing duckbill valve 65 nearest to the ground, optional filter housing 40 and collecting tube 60 are manually pulled apart and disengaged from each other.

Alternatively, projection 35 and collecting tube 60 are manually pulled apart, if the filter is not employed.

A piston and rod combination is provided as an accessory to device 10. The piston is designed to fit within collecting tube 60 and to be placed into uniform flat contact with the entire bottom surface of duckbill valve 65 after cooling sleeve 70 and collecting tube 60 are separated. The rod may be attached to the piston in advance or after insertion of the piston into collecting tube 60. Pressure is then exerted against duckbill valve 65 by means of the rod and piston combination moving duckbill valve 65 vertically upwards through the inside of collecting tube 60 towards open end 75 thereof. Due to the wiper action of Teflon® ring 110, tiny drops of condensate clinging to the walls of collecting tube 60 are collected into a small pool building up around and ahead of Teflon® ring 110. The rod and piston combination are removed from collecting tube 60 when duckbill valve 65 has been moved to within approximately two inches from open end 75 of collecting tube 60. At this point, airtight cap 80 is securely and sealably installed over open end 75 so that collecting tube 60 may be stored and/or shipped to another location, such as a laboratory. By moving duckbill valve 65 towards open end 75, the volume of air within collecting tube 60 is reduced for storage purposes, and the surface area of the condensate which might come into contact with contaminating air is minimized. Alternatively, the movement of duckbill valve 65 within collecting tube 60 can be deferred until after transport. When desired, this piston and rod combination may also serve the additional purpose of providing a degassing mechanism, as discussed below.

Once sealed collecting tube 60 has arrived at a testing location, which may even be at a subject user's home or workplace if diagnostic equipment is stationed there, the collected condensate may be subjected to a variety of treatments depending on the assay desired to be undertaken. Where acidity of the condensate is to be tested or of concern, a degassing or deaeration of the condensate is performed. Degassing or deaerification is a purification process which removes carbon dioxide from the condensate and allows for more accurate and stable measurement of acidity or pH levels. Without this deaeration step, the carbon dioxide in air diffuses in and out of the condensate, changing its pH. This can occur simply as the result of a person breathing over the top of collecting tube 60 when it is open. Thus, any gas that does not contain carbon dioxide or another acid may be used for degassing prior to pH measurement including, but not limited to, argon, helium, oxygen or air that has had carbon dioxide removed from it with a carbon dioxide trap. Alternatively, elimination of carbon dioxide could be accomplished chemically by adding an enzyme and substrate that consumes carbon dioxide and a proton (acid) in a one-to-one ratio.

Figure 6:
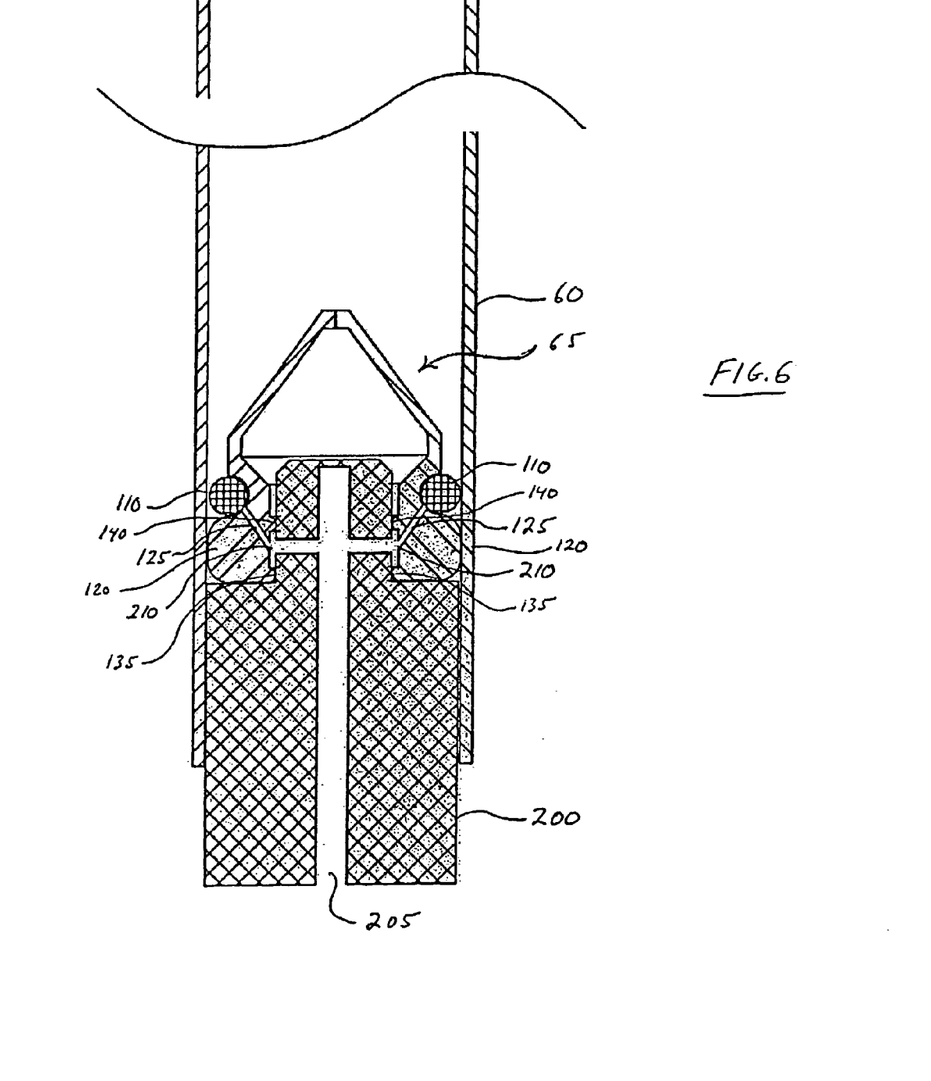
FIG. 6 is a center cross-sectional view of a collecting tube into which a probe has been inserted behind a duckbill valve.

In order to perform degassing on the condensate in sealed collecting tube 60, any one of three methods may be used. First, a probe, which may also serve as the piston discussed previously, may be inserted through the bottom open end of collecting tube 60 and advanced until its further progress is blocked by contact with duckbill valve 65 whereupon pressure is exerted until the nose portion of the probe is seated within duckbill valve 65. Airtight cap 80 should then be removed. Reference is now made to FIG. 6 where a partial cross-sectional view of collecting tube 60 is shown in which probe 200 has been seated within duckbill valve 65. The nose portion of probe 200 has a diameter slightly wider than the diameter of first inner ring 135. In order to seat probe 200, the nose portion is pushed into the hollow center of duckbill valve 65 until further forward movement is impeded by contact between the wider shoulder portion of probe 200 and lower section 120 of duckbill valve 65. At this point, first inner ring 135 has been compacted horizontally so as to form a pressure seal around the nose portion of probe 200 below passageway 125, while second inner ring 140 has also been compacted horizontally to form another pressure seal around the nose portion of probe 200 above passageway 125.

Figure 7:
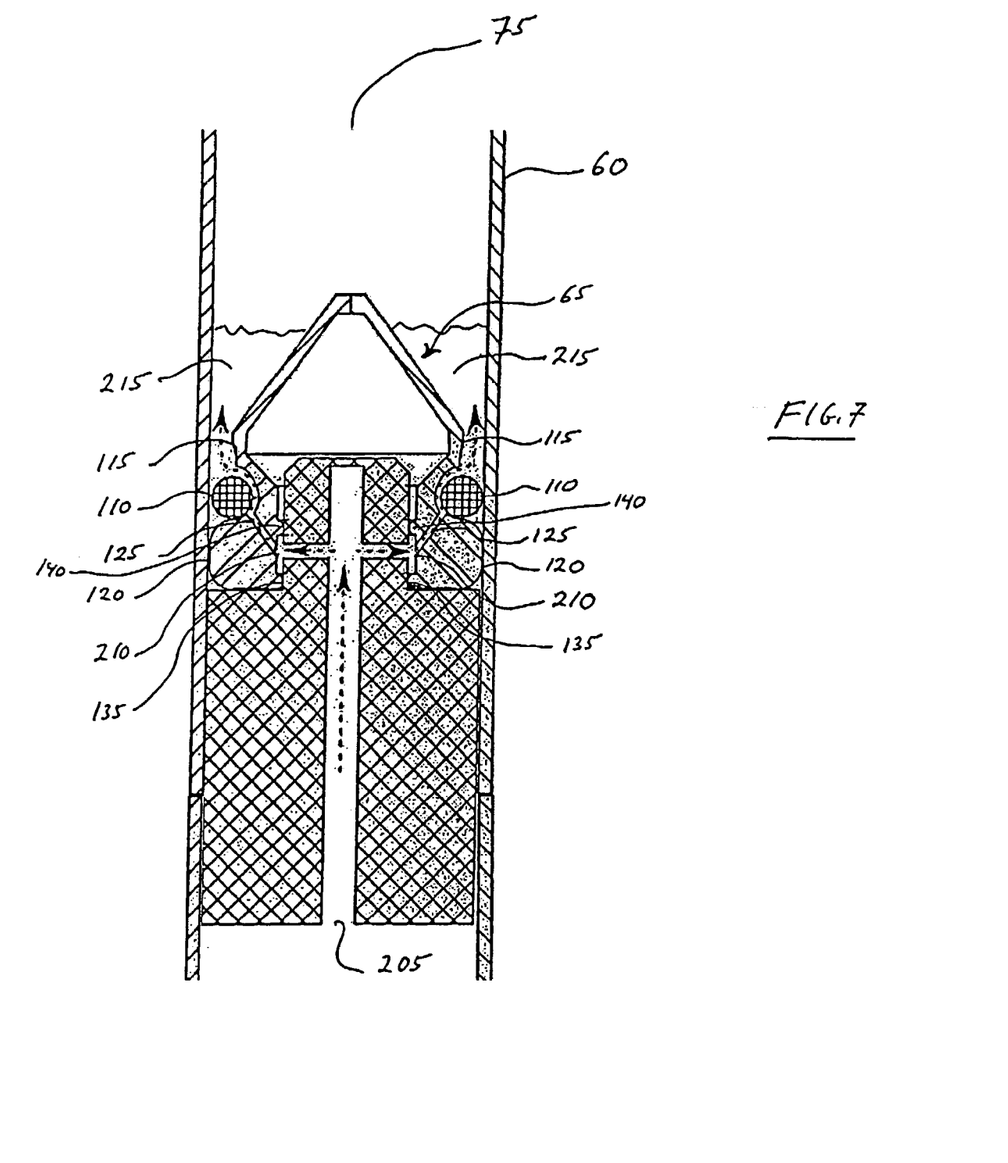
FIG. 7 is a center cross-sectional view of a collecting tube into which gas has been introduced under pressure to degas/deaerate condensate.

Probe 200 includes a hollow, multipath, cylindrical passageway 205 including one or more openings 210 which exit the nose portion of probe 200 at a height equivalent to the location of initiation point 130 within valve 65. Specifically, the location of openings 210 lies between first inner ring 135 and second inner ring 140 inside valve 65. Argon or another carbon dioxide-free gas may be introduced under pressure through passageways 205 of probe 200. As shown in FIG. 7, the pressurized gas follows the path indicated by the dotted lines accompanied by arrows. The mechanical pressure seals formed by inner rings 135 and 140 against the nose portion of probe 200 are considerably stronger than the seal produced by ring 110 against the circular notched area formed on the exterior of duckbill valve 65. Due to the positioning of passageway(s) 125, they are not subjected to stress and exit duckbill valve 65 at a point where the valve is not subjected to mechanical stress. As a result, the pressurized gas introduced through passageways 205 follows the unstressed portion of duckbill valve 65, or passageways 125.

As explained above, upper section 115 tends to deflect when exposed to pressurized gas thereby creating a passageway for the gas to circumvent Teflon® ring 110 and escape into and bubble through condensate 215 pooled in collecting tube 60. Carbon dioxide dissolved in condensate diffuses into the bubbles of the carbon dioxide-free gas. After having passed through condensate 215, the gas, now containing carbon dioxide derived from the condensate is allowed to escape into the atmosphere from collecting tube 60 through now uncapped open end 75. Argon, being heavier than air, assists in preventing carbon dioxide from the ambient air from recontaminating the sample.

An alternative structure for duckbill valve 65 could omit ring 110 and hollow passageways 125 and probe 200. In this case, gas pressure applied into collecting tube 60 below valve 65 by a positive pressure manifold would cause leaves 100 in duckbill valve 65 to open admitting the gas into the condensate pool. The pressure of the gas would prevent condensate from seeping back into the open valve as would the closing bias of leaves 100 when the application of gas pressure terminated. One example of such a manifold would accept the lower end of collecting tube 60, make an airtight seal with it and hold it in a vertical position while forcing gas into the tube for degassing. The manifold could interface with available gas plumbing or hoses connecting to a source of gas.

Figure 8:
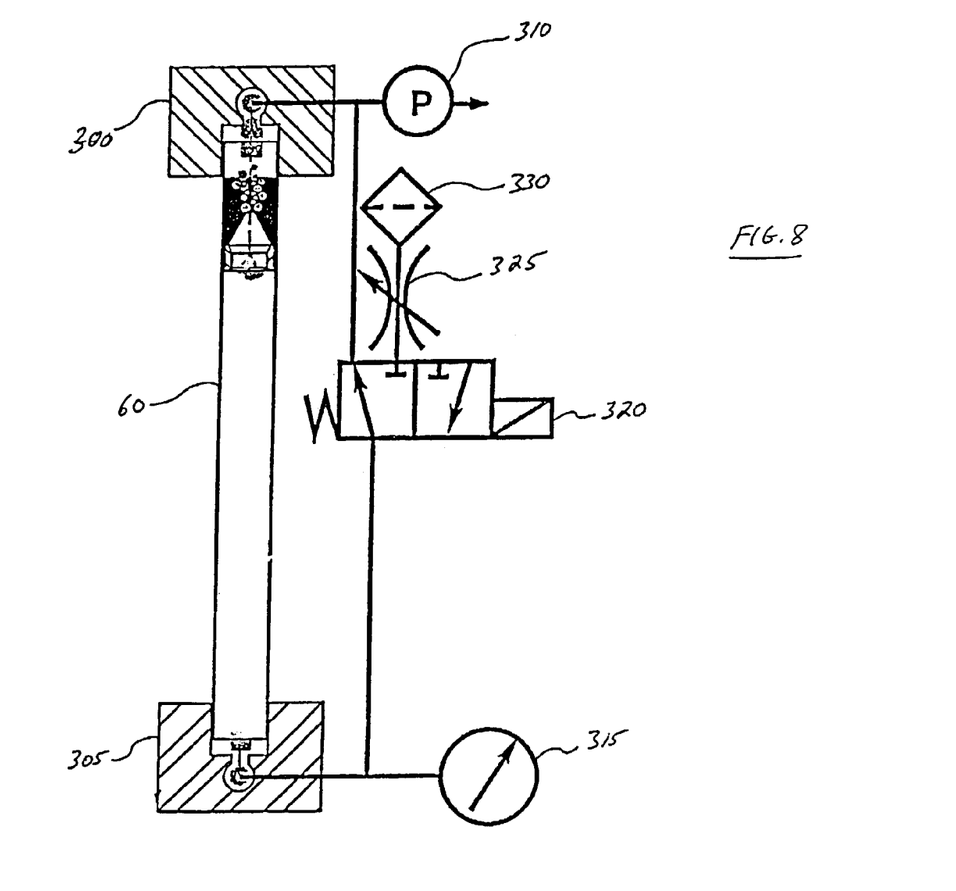
FIG. 8 is a schematic of equipment used in performing a second method of degassing/deaerating.

The third method for degassing is shown in schematic form in FIG. 8. Pursuant to that method, airtight cap 80 is removed from collecting tube 60 which is then inserted into a device enclosing both ends of the tube. A hard vacuum is applied to both ends of the tube and the area of the tube below the duckbill valve is periodically opened to the atmosphere or to a carbon dioxide-free gas source. This procedure draws the carbon dioxide out of the solution in the condensate and allows it to be removed through the vacuum pump. Open end 75 of collecting tube 60 is placed in manifold 300, while the opposing end of the tube is placed in manifold 305. Vacuum pump 310 is attached to open end 75 by means of manifold 300, while vacuum gauge 315 is attached to the opposing end of collecting tube 60 by means of manifold 305. Three-way, two-position solenoid valve 320 is connected between vacuum pump 310 and vacuum gauge 315. An adjustable orifice 325 functioning with solenoid valve 320 is used to regulate the surge of air or other gas into the lower chamber of collecting tube 60, and a filter 330 is connected to adjustable orifice 325 in order to ensure that no contaminants are introduced into the system. A human may be used to determine when to vent the lower part of collecting tube 60 through manifold 305 based on readings from vacuum gauge 315. Alternatively, a vacuum transducer coupled to a controller could be substituted for the vacuum gauge to automate the venting of the collecting tube by energizing solenoid valve 320 pursuant to a control algorithm.

Certain tests might require passing other gases through or adding liquids or solids to the condensate. The same structures and procedures described above may be used to collect, transport, store and otherwise accomplish these tasks. Other tests that might be performed on collected samples include assays for inorganic and organic compounds, including but not limited to amino acids, volatile organic compounds, lipids and lipid oxidation products, ammonia, simple ions such as sodium and chloride, strong and weak acids and bases, surfactant, inflammatory mediators including cytokines and leukotrienes, oxidation and nitration products including hydrogen peroxide and nitrotyrosine, nucleic acids such as DNA and RNA, endotoxin and other microbial products. In addition, it is important to note that the entire cycle of sampling, storage, degassing and much, if not all, of the analysis is done within device 10. Transfer of fluid to other apparati is not generally required. Furthermore, all wetted parts of device 10 can easily be made disposable to minimize contamination, cleaning, and cost. The device is fully portable and can be used even by small children. In an alternative structure, a filter may be positioned on top of collecting tube 60 to prevent infectious particles from escaping while allowing larger particles to be trapped in collecting tube 60. Finally, the device and method of this invention may be adapted for animal use in veterinarian applications.

When the collected condensate sample has been prepared for testing as required, either by degassing or by addition of gas, liquid or another substance, a probe may be inserted through open end 75 to remove a sample of the condensate for testing purposes. Alternatively, the testing can be performed directly within collecting tube 60. For example, after degassing, a calibrated pH probe attached to a pH meter can be immersed in the collected sample to determine sample pH. The sample may be removed by contact with the probe or by suction action through the probe. In other embodiments, chemicals can be added, or a chemically impregnated reagent strip can be immersed into the sample for colorimetric determination of pH and other characteristics and substances.

The foregoing invention has been described in terms of the preferred embodiment. However, it will be apparent to those skilled in the art that various modifications and variations can be made to the disclosed method and system without departing from the scope or spirit of the invention. The specification and examples are exemplary only, while the true scope of the invention is defined by the following claims.

What is claimed is:

1. A method for collecting condensate from the breath of a subject inhaled through and exhaled into a portable device comprising a mouthpiece including a check valve optionally attached to a filter assembly further attached to the bottom end of a cooled, open-ended, hollow collecting tube close to the bottom end of which a hollow duckbill valve has been inserted so as to make a sealing connection with the interior walls thereof and for analyzing the collected condensate for the presence of one or more selected substances comprising:

sliding a cooling sleeve having a lower temperature than the collecting tube over the collecting tube and placing the cooling sleeve in at least close physical proximity with the collecting tube prior to giving the tube to the subject;

instructing the subject to inhale through the mouthpiece while ensuring by means of operation of the duckbill valve and a check valve located within the mouthpiece that air inhaled by the subject comes directly from a desired source and does not contaminate the collecting tube;

directing the subject to exhale through the mouthpiece while maintaining the collecting tube oriented approximately perpendicular to the ground;

channeling breath exhaled from the subject by means of closure of the check valve through the filter assembly, if there is one, and the duckbill valve turbulently into the collecting tube;

repeating returning to the instructing step until a period of approximately ten minutes has elapsed from the first inhalation;

removing the cooling sleeve from around the collecting tube and disconnecting the filter, if any, and mouthpiece assembly from the bottom end of the collecting tube;

pushing the duckbill valve along the length of the collecting tube to within approximately two inches of the top end thereof while maintaining the collecting tube oriented approximately perpendicular to the ground so as to wipe condensate from the interior walls of the collecting tube and form a pool of condensate around the base of the duckbill valve;

installing an airtight cap on the top end of the collecting tube if the tube is to be either stored for later use or shipped to another location for analysis;

moving the tube to the analysis site and removing the airtight cap, if one has been installed;

degassing the condensate pool; and withdrawing a test sample of the condensate for analysis.

2. The method of claim 1 wherein withdrawing further comprises:

inserting a test probe through the open top end of the collecting tube;

advancing the test probe until it comes into contact with the condensate pool; and removing the test probe from the collecting tube.

3. The method of claim 1 wherein injecting further comprises using a manual probe to inject the at least one preselected gas or liquid through the duckbill valve.

4. The method of claim 1 wherein degassing further comprises inserting one end of the collecting tube into a single positively pressurized manifold which forces gas into the bottom of the tube and allows it to exhaust to the atmosphere.

5. The method of claim 1 wherein degassing further comprises retainably placing the top and the bottom of the collecting tube into separate manifolds, subjecting both ends of the collecting tube to a mechanized vacuum and periodically exposing the bottom end of the collecting tube to the atmosphere.

6. The method of claim 5 wherein degassing further comprises removing the tube from retention between the two manifolds.

7. The method of claim 1 wherein degassing further comprises:
- inserting a probe into the bottom end of the tube and advancing the probe until it comes into seated contact with the bottom of the duckbill valve while maintaining the tube oriented approximately perpendicular to the ground;
- injecting at least one preselected gas or liquid under pressure through the duckbill valve into the condensate pool; and
- permitting the preselected gas, if any, to bubble through the condensate and escape into the atmosphere through the open end of the collecting tube or the preselected liquid, if any, to mix with the condensate.

8. A method for collecting condensate from the breath of a subject exhaled into a cooled, hollow collecting tube close to one end of which a one-way valve for admitting breath into the tube has been inserted so as to make a sealing connection with the interior walls thereof comprising:
- admitting exhaled breath into the collecting tube through the one-way valve;
- causing turbulence in the exhaled breath as it is admitted into the collecting tube through the one-way valve to enhance condensation efficiency along the interior walls of the collecting tube;
- moving the one-way valve towards the opposite end of the collecting tube to swipe condensate from the interior walls of the tube and to concentrate and pool the condensate within the collecting tube;
- removing the pooled condensate from the collecting tube or assaying samples of the pooled condensate directly within the collecting tube, whichever is preferred.

9. The method of claim 8 wherein, instead of removing or assaying the pooled condensate, the method further comprises:
- placing an airtight cap sealingly over the opposite end of the collecting tube; and
- either storing the collecting tube in a cooling device at a temperature necessary to maintain the condensate or shipping the collecting tube to another location while maintaining the collecting tube at a temperature necessary to maintain the condensate, whichever is preferred.

10. The method of claim 8 wherein moving further comprises employing a piston and rod type plunger to exert force against the one-way valve to cause motion towards the opposite end of the collecting tube.

11. The method of claim 8 wherein the tube is either portable or disposable or both portable and disposable.

12. A method for collecting condensate from the breath of a subject exhaled into a cooled, hollow collecting tube close to one end of which a one-way valve for admitting breath into the tube has been inserted so as to make a sealing connection with the interior walls thereof comprising:
- moving the one-way valve towards the opposite end of the collecting tube after a subject has exhaled through the one-way valve into the collecting tube to swipe condensate from the interior walls of the tube and to concentrate and pool the condensate within the collecting tube; and
- removing the pooled condensate from the collecting tube or assaying samples of the pooled condensate directly from the collecting tube, whichever is preferred.

13. The method of claim 12 wherein the one-way valve is a duckbill valve.

14. The method of claim 12 wherein the tube is either portable or disposable or both portable and disposable.

15. A method for collecting breath condensate of a subject from an open-ended, hollow, cooled, collecting tube having a one-way valve situated at one end thereof comprising:
- causing the subject to exhale into the collecting tube through the one-way valve and
- swiping the interior walls of the collecting tube from one end to the opposite end thereof with the one-way valve wherein the one-way valve functions as a plunger.

16. The method of claim 15 wherein the plunger is a piston and rod.

17. The method of claim 15 wherein the tube is either portable or disposable or both portable and disposable.

* * * * *